US012648755B2

(12) United States Patent
Beacham et al.

(10) Patent No.: US 12,648,755 B2
(45) Date of Patent: Jun. 9, 2026

(54) TWO-WAY HAPTIC SENSING FOR ROBOTIC ULTRASOUND SCANNING

(71) Applicant: GE Precision Healthcare LLC, Waukesha, WI (US)

(72) Inventors: Jimmie Autrey Beacham, West Allis, WI (US); Katelyn Rose Nye, Glendale, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 18/787,112

(22) Filed: Jul. 29, 2024

(65) Prior Publication Data

US 2026/0026782 A1      Jan. 29, 2026

(51) Int. Cl.
*A61B 8/00*          (2006.01)
*G16H 40/67*          (2018.01)

(52) U.S. Cl.
CPC .......... *A61B 8/4218* (2013.01); *A61B 8/4281* (2013.01); *A61B 8/4444* (2013.01); *A61B 8/467* (2013.01); *A61B 8/5207* (2013.01); *A61B 8/54* (2013.01); *G16H 40/67* (2018.01)

(58) Field of Classification Search
CPC ... A61B 8/4218; A61B 8/4281; A61B 8/4444; A61B 8/467; A61B 8/5207; A61B 8/54; G16H 40/67
See application file for complete search history.

(56) References Cited

U.S. PATENT DOCUMENTS

| | | | |
|---|---|---|---|
| 6,425,865 B1* | 7/2002 | Salcudean .............. | A61B 34/32 600/437 |
| 8,930,027 B2 | 1/2015 | Schaible et al. | |
| 11,446,002 B2 | 9/2022 | Beacham et al. | |
| 2010/0262008 A1 | 10/2010 | Roundhill | |
| 2013/0085387 A1* | 4/2013 | Chen .................... | A61B 8/4218 600/407 |

(Continued)

FOREIGN PATENT DOCUMENTS

WO          2023202420          10/2023

OTHER PUBLICATIONS

Bucolo et al. "Force Feedback Assistance in Remote Ultrasound Scan Procedures," Energies, MDPI, Jul. 2020, 16 pgs.

(Continued)

*Primary Examiner* — Alexei Bykhovski
(74) *Attorney, Agent, or Firm* — Fletcher Yoder, P.C.

(57)          ABSTRACT
A system includes an ultrasound device including an ultrasound probe, a robot including an arm configured to couple to the ultrasound probe, and a reverse collaborative robot configured to be manipulated by a user. The reverse collaborative robot includes actuators to provide haptic feedback to the user. The system includes a control system configured to receive input from a user to begin an ultrasound scan of a subject utilizing the robot to move the ultrasound probe along an acquisition surface of the subject, wherein the user is located at the location remote from the ultrasound device and the robot. The system includes a feedback device disposed on or handled by a subject being imaged by the ultrasound device, wherein the feedback device is configured to receive input to adjust a pressure applied to an acquisition surface of the subject being imaged by the ultrasound probe.

20 Claims, 11 Drawing Sheets

(56) References Cited

U.S. PATENT DOCUMENTS

| | | | |
|---|---|---|---|
| 2014/0058264 A1* | 2/2014 | Baym | A61B 8/4477 |
| | | | 600/447 |
| 2018/0279993 A1 | 10/2018 | Crawford et al. | |
| 2021/0077069 A1* | 3/2021 | Beacham | A61B 8/085 |
| 2021/0128099 A1* | 5/2021 | Al-Noor | A61B 8/54 |
| 2025/0029509 A1* | 1/2025 | Hahn | G16H 40/63 |

OTHER PUBLICATIONS

Bucolo et al., "Remote Ultrasound Scan Procedures with Medical Robots: Towards New Perspectives between Medicine and Engineering," Hindawi Applied Bionics and Biomechanics, Feb. 2022, 12 pgs.
https://youtu.be/xY6GbsfkUl4; accessed Jul. 28, 2024.
https://www.wosler.ca/?_sm_nck=1; accessed Jul. 28, 2024.
https://www.adechotech.com/; accessed Jul. 28, 2024.
https://www.accessdata.fda.gov/cdrh_docs/pdf16/K161354.pdf; accessed Jul. 28, 2024.
https://slideplayer.com/slide/4563743/; accessed Jul. 28, 2024.
https://www.facebook.com/woslerdiagnostics/videos/we-are-excited-to-report-even-more-exciting-news-for-woslers-technology-progress/2853216554808588/; Nov. 28, 2022.
https://www.kinovarobotics.com/resource/a-remote-telerobotic-ultrasound-solution; May 16, 2023.
Kinovar Startup Story: Wosler Diagnostics—Remote Telerobotic Ultrasound Solution, Surgical Robotics Technogology, Apr. 2023, 11 pgs.
Pristina Dueta Hand-held Remote, 2024, 9 pgs.

* cited by examiner

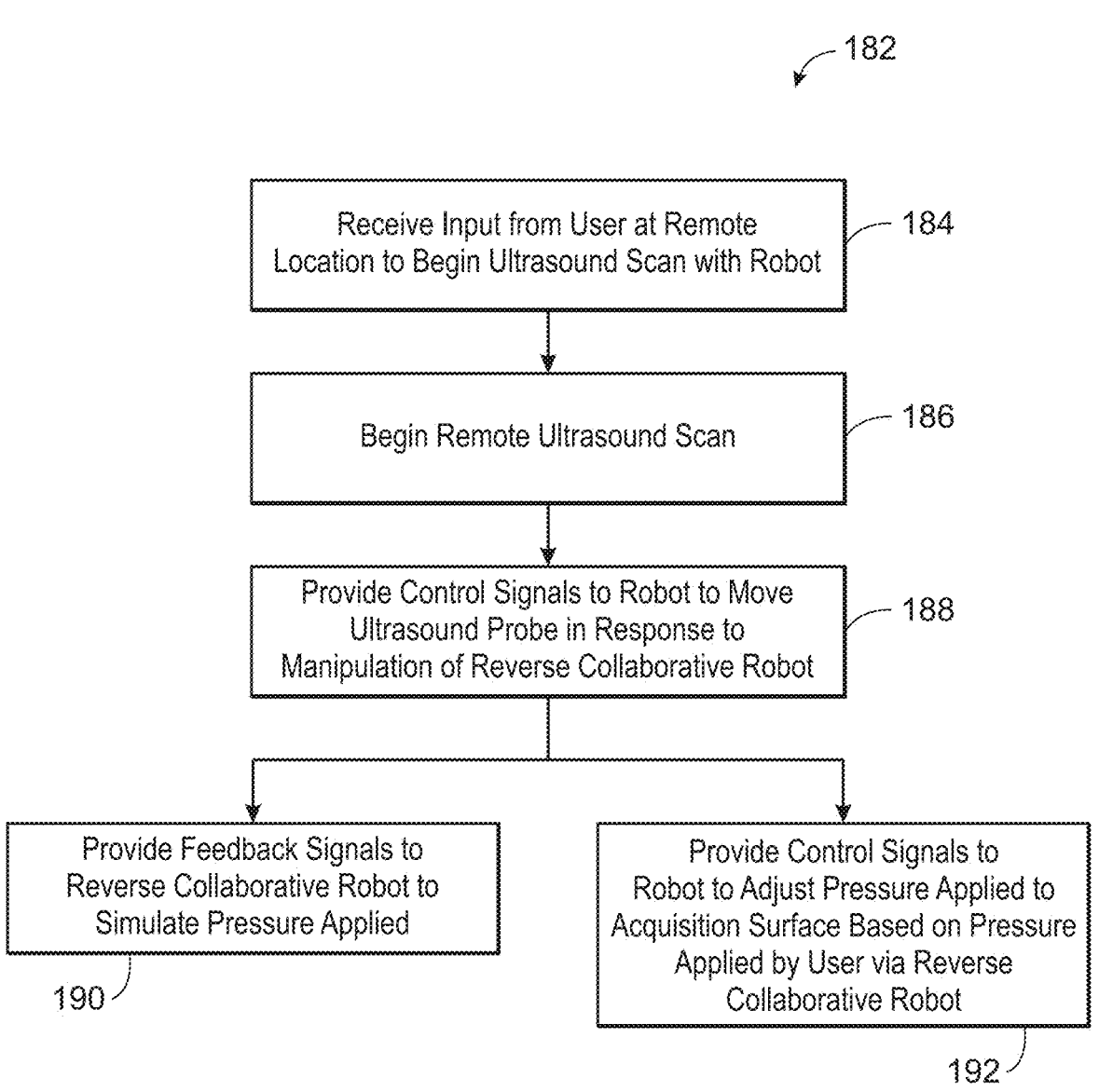

182

Receive Input from User at Remote
Location to Begin Ultrasound Scan with Robot — 184

Begin Remote Ultrasound Scan — 186

Provide Control Signals to Robot to Move
Ultrasound Probe in Response to
Manipulation of Reverse Collaborative Robot — 188

Provide Feedback Signals to
Reverse Collaborative Robot to
Simulate Pressure Applied

190

Provide Control Signals to
Robot to Adjust Pressure Applied to
Acquisition Surface Based on Pressure
Applied by User via Reverse
Collaborative Robot

Receive Input from User at Remote Location to Begin Ultrasound Scan with Robot   — 196

Begin Remote Ultrasound Scan   — 198

Utilize Machine Learning to Provide Control Signals to Robot to Move Ultrasound Probe   — 200

242

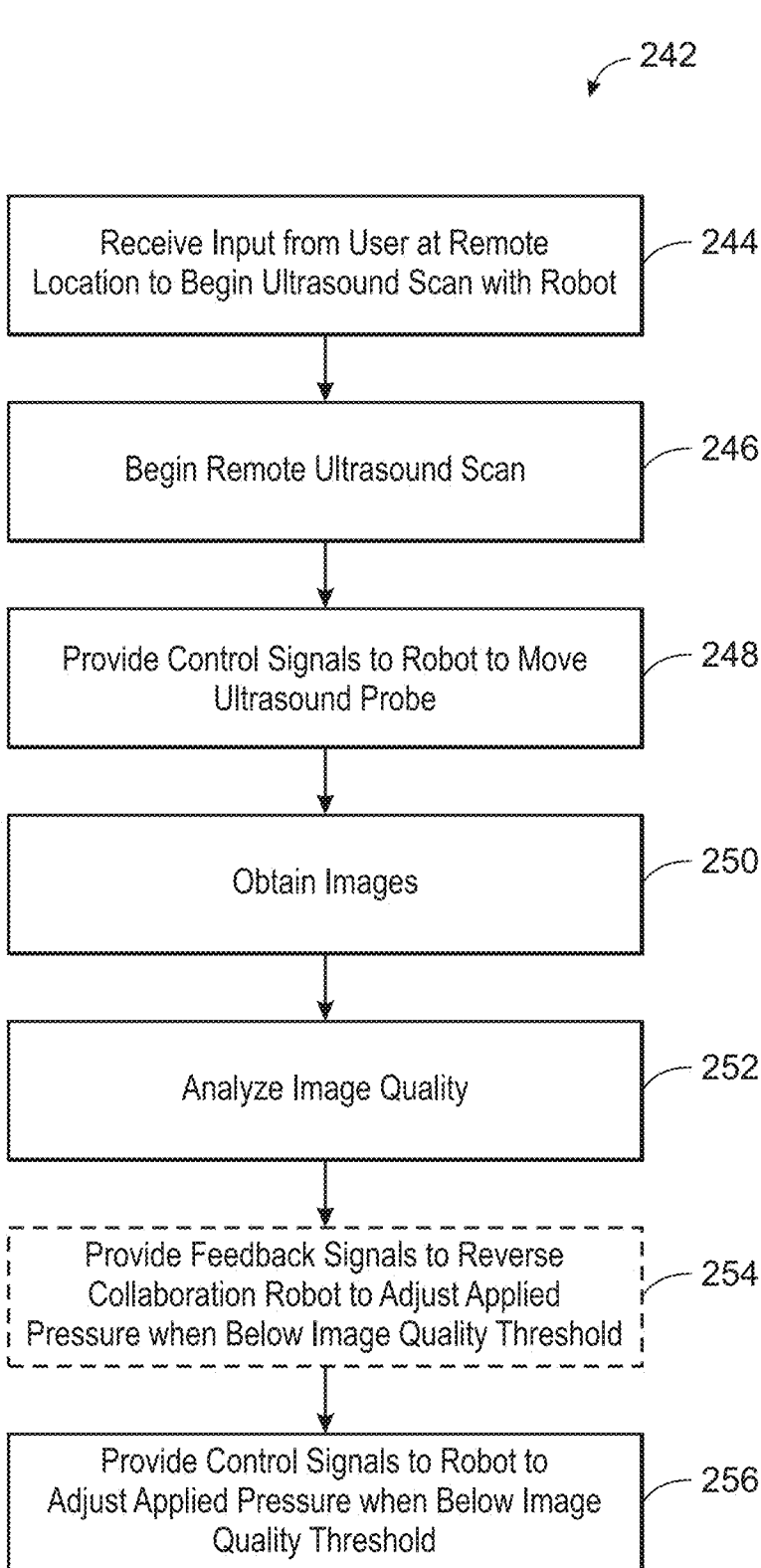

Receive Input from User at Remote Location to Begin Ultrasound Scan with Robot — 244

Begin Remote Ultrasound Scan — 246

Provide Control Signals to Robot to Move Ultrasound Probe — 248

Obtain Images — 250

Analyze Image Quality — 252

Provide Feedback Signals to Reverse Collaboration Robot to Adjust Applied Pressure when Below Image Quality Threshold — 254

Provide Control Signals to Robot to Adjust Applied Pressure when Below Image Quality Threshold — 256

FIG. 9

TWO-WAY HAPTIC SENSING FOR ROBOTIC ULTRASOUND SCANNING

BACKGROUND

The subject matter disclosed herein relates to ultrasound imaging and, more particularly, two-way haptic sensing for robotic ultrasound scanning.

An ultrasound device may be used for imaging targets such as organs and soft tissues in a human body, as well non-human targets. For example, an ultrasound device may be used for applications such as ultrasound/acoustic sensing, non-destructive evaluation (NDE), ultrasound therapy (e.g., High Intensity Focused Ultrasound (HIFU)), etc., in addition to ultrasound imaging of humans, animals, etc.

Ultrasound devices may use real time, non-invasive high frequency sound waves to produce a series of two-dimensional (2D) and/or three-dimensional (3D) images. The sound waves may be transmitted by a transmit transducer, and the reflections of the transmitted sound waves may be received by a receive transducer. The received sound waves may then be processed to display an image of the target. These images may be analyzed. However, specialized clinicians are needed for ultrasound procedures but more remote areas may lack these specialized clinicians.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a system is provided. The system includes an ultrasound device including an ultrasound probe. The system also includes a robot including an arm configured to couple to the ultrasound probe. The system further includes a reverse collaborative robot configured to be manipulated by a user, wherein the reverse collaborative robot is located at a location remote from both the ultrasound device and the robot, and wherein the reverse collaborative robot includes actuators configured to provide haptic feedback to the user. The system includes a feedback device disposed on or handled by a subject being imaged by the ultrasound device, wherein the feedback device is configured to receive input to adjust a pressure applied to an acquisition surface of the subject being imaged by the ultrasound probe. The system even further includes a control system including a processing system and memory, wherein the control system is configured to perform actions. The actions include receiving input from a user, via a user interface, to begin an ultrasound scan of a subject utilizing the robot to move the ultrasound probe along the acquisition surface of the subject, wherein the user is located at the location remote from both the ultrasound device and the robot. The actions also include providing control signals to the robot to move the ultrasound probe along the acquisition surface during the ultrasound scan to acquire ultrasound scan data in response to manipulation of the reverse collaborative robot by the user. The actions further include providing feedback signals to the reverse collaborative robot or user interface to change a pressure applied to the acquisition surface of the subject by the ultrasound probe.

In another embodiment, a system is provided. The system includes an ultrasound device including an ultrasound probe.

The system also includes a robot including an arm configured to couple to the ultrasound probe. The system further includes a control system including a processing system and memory, wherein the control system is configured to perform actions. The actions include receiving input from a user, via a user interface, to begin an ultrasound scan of a subject utilizing the robot to move the ultrasound probe along an acquisition surface of the subject, wherein the user is located at a location remote from both the ultrasound device and the robot. The actions also include utilizing machine learning to provide control signals to the robot to move the ultrasound probe along the acquisition surface during the ultrasound scan to acquire ultrasound scan data free of interaction from the user. The actions further include utilizing machine learning to analyze image quality of images acquired during the ultrasound scan and to provide the control signals, when the image quality is below a predetermined image quality threshold, to the robot to move or to apply more pressure to the ultrasound probe to create full ultrasound probe contact with the acquisition surface In a further embodiment, a method for performing a remote ultrasound exam is provided. The method includes receiving, at a control system having a processing system and memory, input from a user, via a user interface, to begin an ultrasound scan of a subject utilizing a robot having an arm coupled to an ultrasound probe of an ultrasound device to move the ultrasound probe along an acquisition surface of the subject, wherein the user is located at a location remote from both the ultrasound device and the robot. The method also includes providing, via the control system, control signals to the robot to move the ultrasound probe along the acquisition surface during the ultrasound scan to acquire ultrasound scan data in response to manipulation of a reverse collaborative robot by the user, wherein the reverse collaborative robot is located at the location remote from both the ultrasound device and the robot, and wherein the reverse collaborative robot includes actuators configured to provide haptic feedback to the user. The method further includes utilizing, via the control system, machine learning to analyze image quality of images acquired during the ultrasound scan and to provide feedback signals, when the image quality is below a predetermined image quality threshold, to the reverse collaborative robot that cause the actuators to provide an alert to the user to move or to apply more pressure to the ultrasound probe, via the reverse collaborative robot, to create full ultrasound probe contact with the acquisition surface.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein:

FIG. 4 illustrates a flow diagram of a method for performing a remote ultrasound exam (e.g., utilizing a reverse collaborative robot), in accordance with aspects of the present disclosure;

FIG. 9 illustrates a flow diagram of a method for performing a remote ultrasound exam with applied pressure monitoring (e.g., utilizing analysis of image quality), in accordance with aspects of the present disclosure;

DETAILED DESCRIPTION

Figure 1:
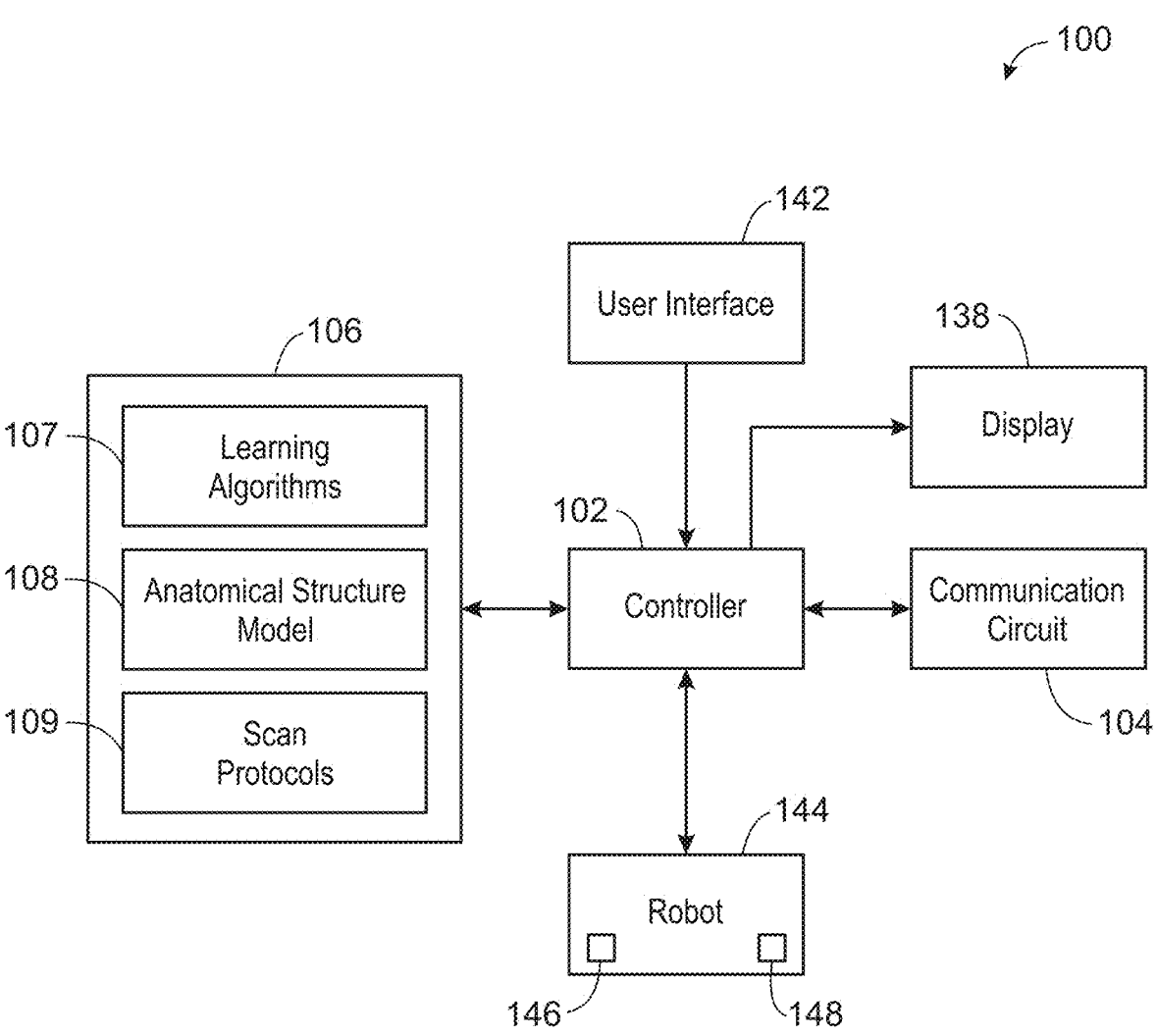
FIG. 1 is a schematic diagram of a medical diagnostic system, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Some generalized information is provided to provide both general context for aspects of the present disclosure and to facilitate understanding and explanation of certain of the technical concepts described herein.

As used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mod014e, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

Patient comfort must be considered with the introduction of new technology within the medical imaging filed, as machines are interfacing with people's bodies in a more automated fashion, which may cause distrust and concern as in the past clinicians and medical technologists were performing such interactions. In the case of a robotic arm driven ultrasound machine, the robot must hold a probe and make contact a person's body with varying levels of applied pressure and locations.

The present disclosure provides systems and methods for remote ultrasound scanning utilizing a robotic system. In particular, two-way haptic sensing for robotic ultrasound scanning may be provided. In certain embodiments, a clinician or medical technologist located remotely (i.e., not in the same room as the patient and possibly many miles away) from both the patient and the ultrasound machine utilizes a reverse collaborative robot to control the ultrasound probe that is in contact with the patient and being moved by a robot having an armed coupled to the ultrasound probe. The reverse collaborative robot simulates the pressure against the clinician's (or medical technologist's) hand that the patient feels on the receiving end as if they were in the same room. In particular, the force, angle, and position of the ultrasound probe measured on the patient side of the system is transmitted to the location of the clinician so that the feedback is in real-time. In certain embodiments, to provide a sense of control and comfort to patients, a feedback device (e.g., remote control) is disposed on or handled by the patient that enables the patient, during the examination, to provide feedback to the robotic system (and possibly the remotely located clinician or medical technologist) indicating if the patient is uncomfortable and wants the examination to stop or force less force/pressure to be applied to their body. In certain embodiments, images may be of higher quality if more pressure/contact is made with the body, and if a patient is comfortable and can withstand additional pressure, they can also such to the robotic system. In certain embodiments, when the clinician is utilizing the reverse collaborative robot remotely, the clinician (via the reverse collaborative robot) may feel an alert if the patient feels discomfort which would serve as a signal to the clinician to back off on the pressure or stop the procedure. In certain embodiments, the robotic system would conduct the ultrasound examination autonomously upon remote initiation by the clinician. The disclosed embodiments provide more access to ultrasound examinations in remote areas where specialized clinicians or medical technologists are not available. The disclosed embodiments also provide the patient with the ability to control their comfort level while also providing an extra layer of safety for remote imaging.

Figure 2:
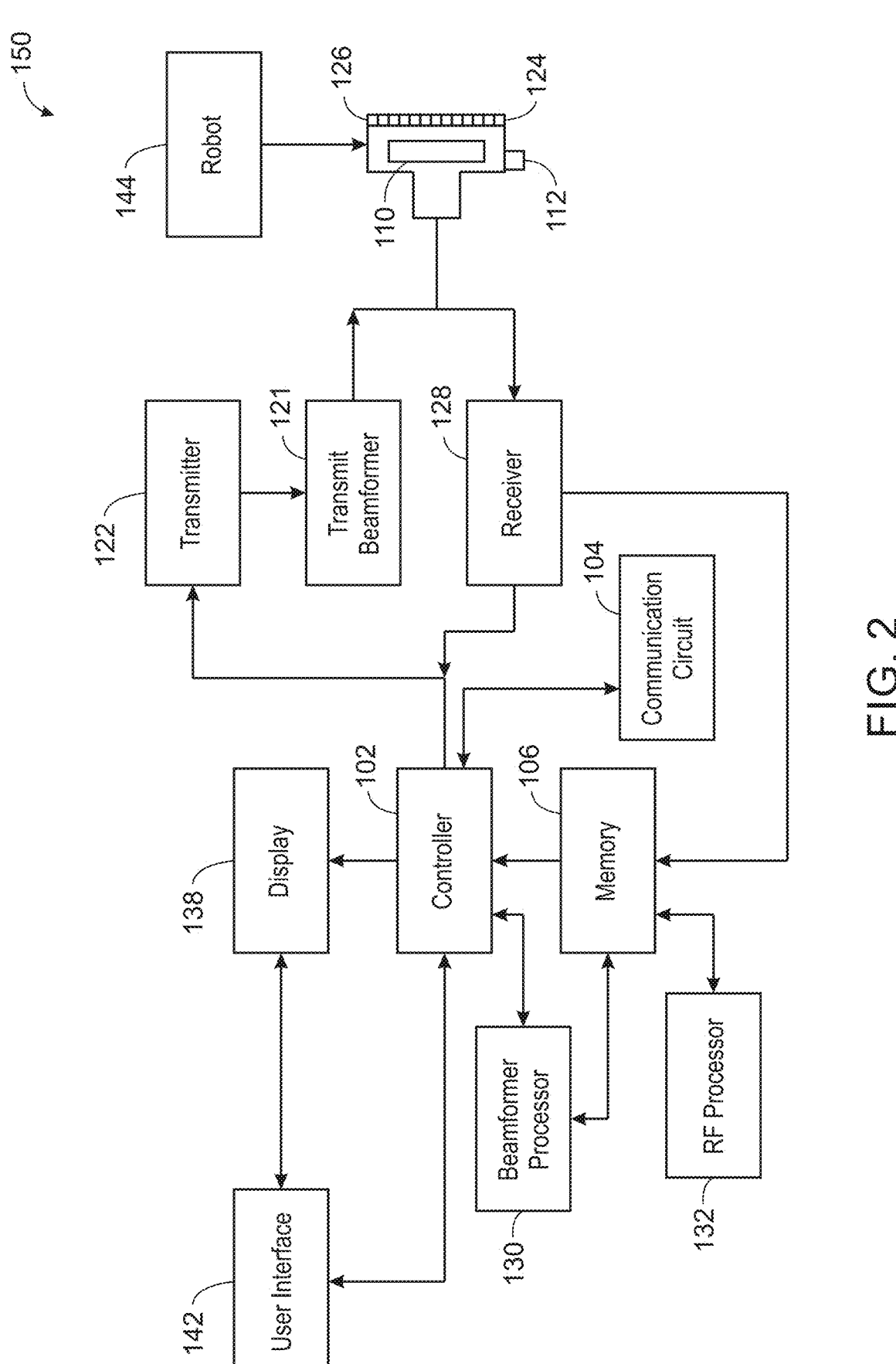
FIG. 2 is a schematic diagram of another medical diagnostic system, in accordance with aspects of the present disclosure.

FIGS. 1 and 2 illustrate schematic block diagrams of first and second embodiments of a medical diagnostic system (MDS) 100, 150, respectively. The MDS 100 of FIG. 1 includes a controller (e.g., controller circuit) 102 operably coupled to a communication circuit 104, a display (e.g., display device) 138, a user interface 142, a robot 144, and a memory 106.

The communication circuit 104 may be communicatively coupled to one or more additional MDS (e.g., such as the MDS 150 shown in FIG. 2), one or more medical diagnostic imaging devices, a remote server, and/or the like via corresponding bi-directional communication links. The one or more medical diagnostic imaging systems may include ultrasound imaging systems or devices, in one example. The remote server may be configured to store sets of medical images from prior scanning and/or clinician sessions of a patient acquired by the one or more medical diagnostic imaging systems.

The bi-directional communication links may be a wired (e.g., via a physical conductor) and/or wireless communication (e.g., utilizing radio frequency (RF)) link for exchanging data (e.g., data packets) between the MDS 100 and the alternative MDS, the one or more medical diagnostic imaging systems, the remote server, and/or the like. For example, the MDS 100 may receive a set of medical images from saved scanning and/or clinician sessions from the alternative MDS, the one or more medical diagnostic imaging systems, the remote server, and/or the like. The set of medical images may include medical imaging data used to generate the images and corresponding position sensor data from a probe used to acquire the medical imaging data, as discussed further herein. The bi-directional communication links may be based on a standard communication protocol, such as Ethernet, transmission control protocol/internet protocol (TCP/IP), WiFi, 802.11, a customized communication protocol, and/or the like.

The controller 102 is configured to control the operation of the MDS 100. The controller 102 may include one or more processors. Optionally, the controller 102 may include a central processing unit (CPU), one or more microprocessors, a graphics processing unit (GPU), or other electronic components capable of processing inputted data according to specific logical instructions stored on a memory of the controller or coupled with the controller. Optionally, the controller 102 may include and/or represent one or more hardware circuits or circuitry that include, are connected with, or that both include and are connected with one or more processors, controllers, and/or other hardware logic-based devices. Additionally or alternatively, the controller 102 may execute instructions stored on a tangible and non-transitory computer readable medium (e.g., the memory 106).

The controller 102 may be operably coupled to and/or control the communication circuit 104. The communication circuit 104 is configured to receive and/or transmit information with the one or more medical diagnostic imaging systems, the alternative MDS, the remote server, and/or the like. The communication circuit 104 may represent hardware that is used to transmit and/or receive data along the bi-directional communication links. The communication circuit 104 may include a transceiver, receiver, etc., and associated circuitry (e.g., antennas) for wired and/or wirelessly communicating (e.g., transmitting and/or receiving) with the one or more medical diagnostic imaging systems, the alternative MDS, the remote server, and/or the like. For example, protocol firmware may be stored in the memory 106, which is accessed by the controller 102. The protocol firmware provides the network protocol syntax for the controller 102 to assemble data packets, establish and/or partition data received along the bi-directional communication links, and/or the like.

The controller 102 is operably coupled to the display 138 and the user interface 142. The display 138 may include one or more liquid crystal displays (e.g., light emitting diode (LED) backlight), organic light emitting diode (OLED) displays, plasma displays, cathode ray tube (CRT) displays, and/or the like. The display 138 may display patient information, one or more medical images and/or videos, components of a graphical user interface, one or more 2D, 3D, or 4D ultrasound image data sets from ultrasound data stored in the memory 106 or currently being acquired, measurements, diagnosis, treatment information, alerts or indications, directions, and/or the like received by the display 138 from the controller circuit 102.

The user interface 142 controls operations of the controller 102 and is configured to receive inputs from the user. The user interface 142 may include a keyboard, a mouse, a touchpad, one or more physical buttons, and/or the like. Optionally, the display 138 may be a touch screen display, which includes at least a portion of the user interface 142. For example, a portion of the user interface 142 may correspond to a graphical user interface (GUI) generated by the controller 102, which is shown on the display 138. The touch screen display can detect a presence of a touch from the operator on the display 138 and can also identify a location of the touch with respect to a surface area of the display 138. For example, the user may select one or more user interface icons of the GUI shown on the display by touching or making contact with the display 138. The touch may be applied by, for example, at least one of an individual's hand, glove, stylus, or the like.

The memory 106 includes instructions, parameters, algorithms, models, data values, and/or the like utilized by the controller 102 to perform one or more operations described herein. The memory 106 may be a tangible and non-transitory computer readable medium such as flash memory, random access memory (RAMI, read-only memory (ROM), electrically erasable programmable read-only memory (EEPROM), and/or the like. The memory 106 may include a set of machine learning algorithms 107 (e.g., convolutional neural network algorithms, deep learning algorithms, decision tree learning algorithms, and/or the like) configured to define a plurality of scan protocols 109 and an anatomical structure model 108. Additionally or alternatively, the scan protocols 109 and/or the anatomical structure model 108 may be received along one of the bi-directional communication links via the communication circuit 104 and stored in the memory 106.

For example, the anatomical structure model 108 may be defined by the machine learning algorithms 107 to identify one or more anatomical structures of interest (e.g., reference points) based on features of the one or more anatomical structures (e.g., boundaries, thickness, and/or the like) within the one or more medical images. The features may represent high level features of the pixels and/or voxels of the medical image such as a histogram orient gradients, blob features, covariance features, binary pattern features, and/or the like. Optionally, the machine learning algorithm 107 may define the anatomical structure model 108 by automatically building a statistical model and/or a database of true positives and true negatives corresponding to each anatomical structure identified based on the features from a set of training images, a classification model, supervised modeling, and/or the like.

In certain embodiments, the machine learning algorithms 107 provide control signals to the robot (and reverse collaborative robot) to move the ultrasound probe along the acquisition surface during the ultrasound scan to acquire ultrasound scan data free of interaction from the user. In certain embodiments, the machine learning algorithms 107 analyze image quality of images acquired during the ultrasound scan and to provide the control signals, when the image quality is below a predetermined image quality threshold, to the robot (and reverse collaborative robot) to move or to apply more pressure to the ultrasound probe to create full ultrasound probe contact with the acquisition surface. In certain embodiments, the machine learning algorithms 107 analyze image quality of images acquired during the ultrasound scan and to provide a control signal, when the image quality is below a predetermined image quality threshold, to the automatic ultrasound conductive gel dispenser to apply conductive gel to the acquisition surface of the subject.

For example, the anatomical structure model 108 may be configured and/or designed based on a plurality of training medical images and/or a plurality of scan protocols. The plurality of scan protocols may be grouped into different anatomical structure sets, such as organs (e.g., heart, kidney, liver, bladder, lung, brain, and/or the like), skeletal structures (e.g., bone, skull, and/or the like), vascular structures (e.g., artery, vein, and/or the like), regions of a body (e.g., head, torso, and/or the like), and/or the like.

Additionally or alternatively, the anatomical structure model 108 may be defined based on a supervised learning method. For example, a user (e.g., skilled medical practitioner) may manually label the one or more anatomical structures within the plurality of training medical images utilizing the user interface 142 and an ultrasound probe (e.g., ultrasound probe 126 of FIG. 2) and the robot 144. The manually labeled medical images may be used to build a statistical model and/or a database of true positives and true negatives corresponding to each anatomical structure defining the anatomical structure model 108.

The plurality of scan protocols 109 are configured to define a sequence of scans to generate a desired ultrasound image. The desired ultrasound image may comprise a plurality of ultrasound images combined to produce a three-dimensional view of an anatomical region. Each scan protocol of the plurality of scan protocols 109 may comprise one or more travel paths along with one or more forces. The one or more forces comprise at least a probe force and/or an interface force, which may correspond to a force at which the probe is pressed against an acquisition surface (e.g., a patient's skin). The probe force may occur at a plurality of angles relative to the acquisition surface, wherein the plurality of angles may also be stored with a corresponding travel path profile of a single scan protocol. The travel path profile may further comprise a velocity at which to move the ultrasound probe along the travel path. The entirety of the scan protocol may be learned via the robot 144. In one example, the robot 144 is a collaborative robot.

For example, if the desired anatomical region is the head, then the robot 144 may learn to scan structures within the head, wherein features of the head (e.g., eye socket, internal bone structure, thickness, shape, and/or the like) are identified within the medical image as a check to ensure the robot 144 is correctly traveling along the travel path. The features may be based on high level features of the pixels and/or voxels of the medical image such as a histogram orient gradients, blob features, covariance features, binary pattern features, and/or the like.

In one embodiment, the user may actuate a probe (e.g., probe 126 of FIG. 2), to which an arm of the robot 144 may be coupled. As the probe is actuated, memory 106 may be updated, including the learning algorithms, the anatomical structure model 108, and the scan protocols 109. Specifically, the scan protocols 109 may comprise a plurality of travel path profiles, each corresponding to an ultrasound scan sequence for a specific anatomical region or an ultrasound scan type (e.g., fetal scan type, kidney scan type, etc.). Each travel path profile may comprise a set of forces and a set of positions at which to apply one or more forces at one or more angles. Each travel path profile may further comprise a velocity at which it is desired for the robot 144 to actuate the ultrasound probe along the travel path. The robot 144 may comprise a plurality of sensors 146 and actuators 148, which may provide feedback a force of movement of an appendage of the robot 144 along with other feedback.

In this way, the learning algorithms 107, anatomical structure model 108, and scan protocols 109 may together form instructions executed by the controller 102 and signaled to the robot 144 to acquire an ultrasound image with inputs from a user. The images and/or image data may be classified by scan plane of an anatomical structure and/or by anatomical landmark/structure such that a target or desired scan plane or anatomical structure is identified by the controller, using the stored models and/or algorithms. The identified target scan plane(s) of an anatomical structure and/or an anatomical structure may then be displayed to a user via the display 138. In this way, the user may be able to visualize in real-time if the robot 144 is accurately acquiring a desired ultrasound image. Furthermore, the identification of the various landmarks and/or structures (e.g., reference points) may enable the controller to adjust an operation of the robot 144 (e.g., a force applied to the acquisition surface and/or an orientation of the probe relative to the acquisition surface) in response to a currently acquired image not matching a previously acquired image. Such a mismatch may occur due to variability between patients due to height, weight, and other differences. However, by allowing the robot 144 to follow a general learned travel path, a direction, length, and location of the travel path may be substantially similar across a broad spectrum of patients.

Turning to FIG. 2, the MDS 150 may be integrated with and/or a part of a medical diagnostic imaging system. For example, the MDS 150 includes an ultrasound imaging system. The MDS 150 includes an ultrasound probe 126 having a transmitter 122, transmit beamformer 121, probe/system, applications, and products (SAP) electronics 110, and a position sensor 112. The probe/SAP electronics 110 may be used to control the switching of the transducer elements 124. The probe/SAP electronics 110 may also be used to group transducer elements 124 into one or more sub-apertures.

The ultrasound probe 126 may be configured to acquire ultrasound data or information from the anatomical structures (e.g., organ, blood vessel, heart) of the patient based on the predetermined settings. Additionally, the ultrasound probe 126 may acquire position information (e.g., data), via the position sensor 112, that includes the spatial position, relative to a coordinate system and a reference point which may be predefined by the controller, of the probe 126. The position data may correspond to the acquired ultrasound image data, such that each image (or scanned image plane or frame) includes a corresponding position of the probe at the time the image data was acquired. The position data may be further indexed with one or more learned robot actions. For example, as a user moves the ultrasound probe 126 and adjusts an orientation of the probe or a probe pressure applied at an interface between the probe and an acquisition surface, feedback regarding the orientation and the probe pressure may be stored with a corresponding position of the probe such that the robot 144 may replicate the orientation and the probe pressure at the position during a future ultrasound acquisition without external force being provided by the user. In certain embodiments, upon training of the robot 144, the robot 144 may be utilized to conduct ultrasound exams autonomously upon remote initiation by a user as described in greater detail below.

The ultrasound probe 126 is communicatively coupled to the controller 102 via the transmitter 122. The transmitter 122 transmits a signal to at transmit beamformer 121 based on acquisition settings received by the controller 102. The acquisition settings may define an amplitude, pulse width, frequency, gain setting, scan angle, power, time gain compensation (TGC), resolution, and/or the like of the ultrasonic pulses emitted by the transducer elements 124. The probe 126 may include an additional transmitter for transmitting the signals formed by the transmit beamformer 121. The transducer elements 124 emit pulsed ultrasonic signals into a patient (e.g., a body). The acquisition settings may be defined by the user utilizing the user interface 142. The signal transmitted by the transmitter 122 in turn drives a plurality of transducer elements 124 within a transducer array.

The transducer elements 124 emit pulsed ultrasonic signals into a body (e.g., patient) or volume corresponding to the acquisition settings along one or more scan planes. The ultrasonic signals may include, for example, one or more reference pulses, one or more pushing pulses (e.g., shearwaves), and/or one or more pulsed wave Doppler pulses. At least a portion of the pulsed ultrasonic signals back-scatter from the anatomical structures (e.g., heart, left ventricular outflow tract, breast tissues, liver tissues, cardiac tissues, prostate tissues, neonatal brain, embryo, abdomen, and the like) to produce echoes. The echoes are delayed in time and/or frequency according to a depth or movement, and are received by the transducer elements 124 within the transducer array of the probe 126. The ultrasonic signals may be used for imaging, for generating and/or tracking shearwaves, for measuring changes in position or velocity within the anatomic structure, differences in compression displacement of the tissue (e.g., strain), and/or for therapy, among other uses. For example, the probe 126 may deliver low energy pulses during imaging and tracking, medium to high energy pulses to generate shear-waves, and high energy pulses during therapy.

The transducer elements 124 convert the received echo signals into electrical signals which may be received by a receiver 128. The receiver 128 may include one or more amplifiers, an analog to digital converter (ADC), and/or the like. The receiver 128 may be configured to amplify the received echo signals after proper gain compensation and convert these received analog signals from each transducer element 124 to digitized signals sampled uniformly in time. The digitized signals representing the received echoes are stored in memory 106, temporarily. The digitized signals correspond to the backscattered waves receives by each transducer element 124 at various times. After digitization, the signals still may preserve the amplitude, frequency, phase information of the backscatter waves. The receiver 128 may also transmit positional data, received from the position sensor 112 to the controller 102 and/or memory 106.

Optionally, the controller 102 may retrieve the digitized signals stored in the memory 106 to prepare for the beamformer processor 130. For example, the controller 102 may convert the digitized signals to baseband signals or compressing the digitized signals.

The beamformer processor 130 may include one or more processors. Optionally, the beamformer processor 130 may include a central controller circuit (CPU), one or more microprocessors, or any other electronic component capable of processing inputted data according to specific logical instructions. Additionally or alternatively, the beamformer processor 130 may execute instructions stored on a tangible and non-transitory computer readable medium (e.g., the memory 106) for beamforming calculations using any suitable beamforming method such as adaptive beamforming, synthetic transmit focus, aberration correction, synthetic aperture, clutter reduction and/or adaptive noise control, and/or the like. Optionally, the beamformer processor 130 may be integrated with and/or apart of the controller. For example, the operations described being performed by the beamformer processor 130 may be configured to be performed by the controller 102.

The beamformer processor 130 performs beamforming on the digitized signals of transducer elements and outputs a radio frequency (RF) signal. The RF signal is then provided to an RF processor 132 that processes the RF signal. The RF processor 132 may include one or more processors. Optionally, the RF processor 132 may include a central controller circuit (CPU), one or more microprocessors, or any other electronic component capable of processing inputted data according to specific logical instructions. Additionally or alternatively, the RF processor 132 may execute instructions stored on a tangible and non-transitory computer readable medium (e.g., the memory 106). Optionally, the RF processor 132 may be integrated with and/or apart of the controller 102. For example, the operations described being performed by the RF processor 132 may be configured to be performed by the controller 102.

The RF processor 132 may generate different ultrasound image data types, e.g. B-mode, color Doppler (velocity/power/variance), tissue Doppler (velocity), and Doppler energy, for multiple scan planes or different scanning patterns based on the predetermined settings of the first model. For example, the RF processor 132 may generate tissue Doppler data for multi-scan planes. The RF processor 132 gathers the information (e.g. I/Q, B-mode, color Doppler, tissue Doppler, and Doppler energy information) related to multiple data slices and stores the data information, which may include time stamp and orientation/rotation information, in the memory 106.

Alternatively, the RF processor 132 may include a complex demodulator (not shown) that demodulates the RF signal to form IQ data pairs representative of the echo signals. The RF or IQ signal data may then be provided directly to the memory 106 for storage (e.g., temporary storage). Optionally, the output of the beamformer processor 130 may be passed directly to the controller 102.

The controller 102 may be configured to adjust the system settings, image presentation settings, and/or anatomical structures represented by the ultrasound data and/or ultrasound images acquired by the MDS 150. For example, the controller 102 may be configured to process the acquired ultrasound data (e.g., RF signal data or IQ data pairs) and prepare and/or generate frames of ultrasound image data representing the anatomical structure for display on the display 138. Acquired ultrasound data may be processed in real-time by the controller 102 during a scanning or therapy session as the echo signals are received. Additionally or alternatively, the ultrasound data may be stored temporarily in the memory 106 during a scanning session and processed in less than real-time in a live or off-line operation.

For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation.

The memory 106 may be used for storing processed frames of acquired ultrasound data that are not scheduled to be displayed immediately or to store post-processed images (e.g., shear-wave images, strain images), firmware or software corresponding to, for example, a graphical user interface, one or more default image display settings, programmed instructions, and/or the like. The memory 106 may store 2D and/or 3D ultrasound image data sets of the ultrasound data, where such 2D and/or 3D ultrasound image data sets are accessed to present 2D and 3D images. For example, a 2D or 3D ultrasound image data set may be mapped into the corresponding memory 106, as well as one or more reference planes. The processing of the ultrasound data, including the ultrasound image data sets, may be based in part on user inputs, for example, user selections received at the user interface 142.

The ultrasound imaging system of MDS 150 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 106 is of sufficient capacity to store at least several seconds worth of frames of ultrasound data. The frames of data are stored in a manner to facilitate retrieval thereof according to its order or time of acquisition. The memory 106 may comprise any known data storage medium. In one example, FIGS. 1 and 2 illustrate a system, comprising an ultrasound device comprising an ultrasound probe, a robot configured to couple to the ultrasound probe and a controller with computer-readable instructions stored on non-transitory memory thereof that when executed enable the controller to adjust the robot to a learning mode comprising a velocity control mode and a force control mode, the velocity control mode comprising translating a handle force of the ultrasound probe into a velocity command, the force control mode comprising estimating a probe force applied to an acquisition surface of a patient and adjust the robot to an image acquisition mode in response to an absence of an external force being applied to the ultrasound probe. By doing this, the robot may acquire an ultrasound image independently (e.g., without assistance and/or guidance from a user), which may increase time for the user to conduct other medical activities. Additionally, the robot may decrease variability between ultrasound image acquisitions due to different users (e.g., technicians) using different acquisition techniques. The robot may execute a single scan protocol for each scan protocol type, thereby allowing a user (e.g., a physician) to analyze consistent ultrasound images.

The learning mode further comprises learning one or more travel path profiles specific to an ultrasound scan type, wherein each travel path profile comprises a travel path, one or more velocities, one or more probe forces, and one or more probe orientations. As such, the robot may acquire ultrasound images from various scan planes at various probe forces while maintaining a desired acquisition rate.

The ultrasound scan type may be a scan type including one or more of organs, skeletal structures, vascular structures, and regions of a body. Each scan type comprises different travel path profiles. The image acquisition mode comprises executing the one or more travel path profiles learned in response to the absence of the external force and an input from a user for a selection of the ultrasound scan type. Thus, the robot may adjust starting and ending positions of the ultrasound probe similar to the positions used by the user during the training in order to acquire an ultrasound image closely resembling the ultrasound image acquired during the training.

In one example, the robot is a collaborative robot, the collaborative robot comprising at least one force sensor arranged at a hand, wherein the hand is configured to couple to the ultrasound probe. The force control mode during the learning mode comprises estimating the probe force applied by sensing an amount of motor actuation of one or more motors of the robot, wherein the amount of motor actuation is learned and replicated during the image acquisition mode. The handle force is a force applied to a handle of the ultrasound probe in a direction parallel to the acquisition surface, and wherein the probe force is a force applied at an interface between the ultrasound probe and the acquisition surface, wherein a direction of the probe force is angled to the acquisition surface. A force applied to the handle in a direction angled to the acquisition surface is not translated into the velocity command, wherein the velocity command is proportional to the handle force. In this way, the robot may be responsive to external pressures, such as external pressures applied by the user, a patient, or other source.

In various embodiments of the present invention, one or more components of MDS 150 may be included in a portable, handheld ultrasound imaging device. For example, display 138 and user interface 142 may be integrated into an exterior surface of the handheld ultrasound imaging device, which may further contain controller 102, beamformer processor 130, RF processor 132, and memory 106. Probe 126 may comprise a handheld probe in electronic communication with the handheld ultrasound imaging device to collect raw ultrasound data. Transmit beamformer 121, transmitter 122, and receiver 128 may be included in the same or different portions of the ultrasound imaging system 100. For example, transmit beamformer 121, transmitter 122, and receiver 128 may be included in the handheld ultrasound imaging device, the probe, and combinations thereof.

Figure 3:
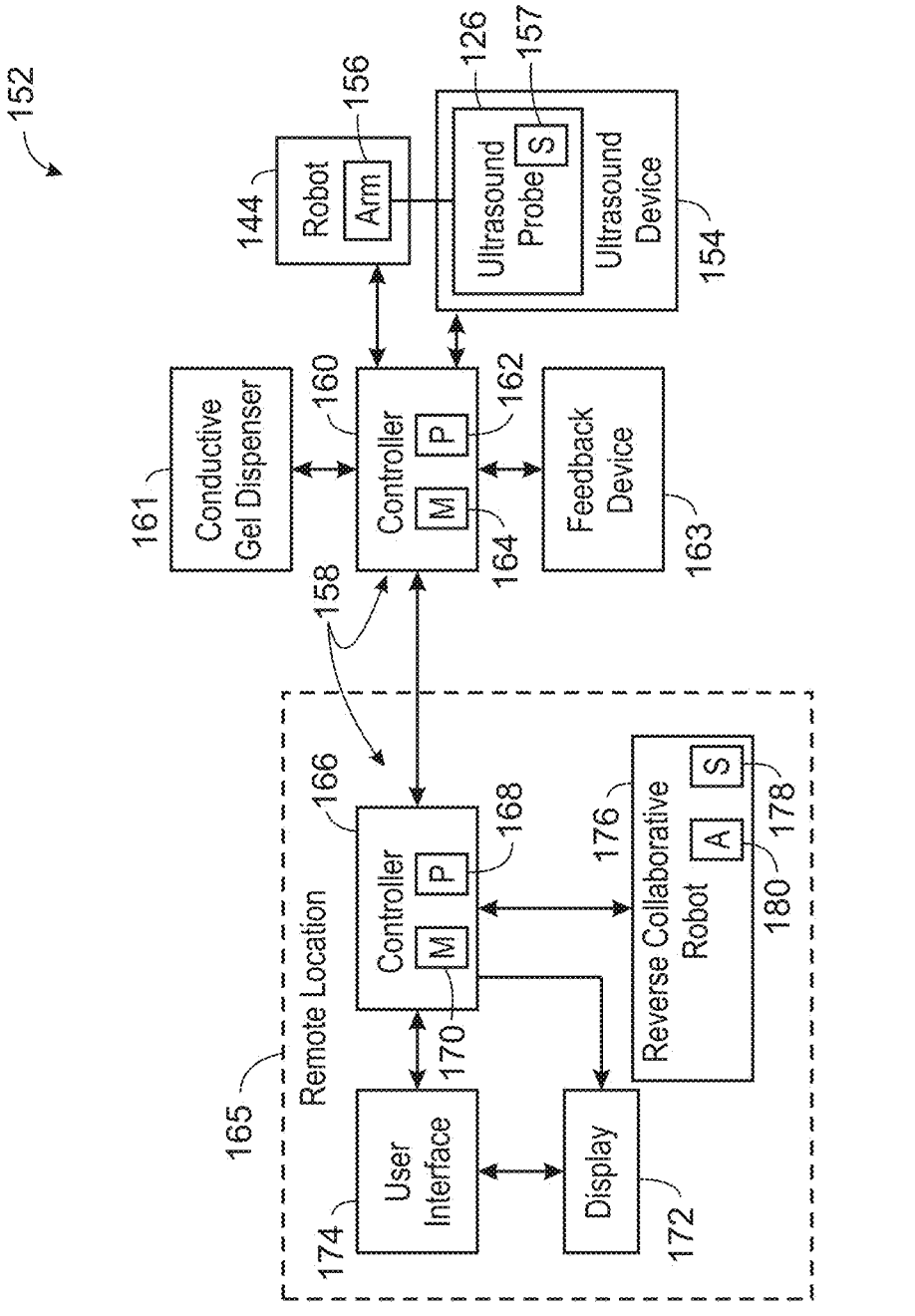
FIG. 3 is a schematic diagram of an ultrasound imaging system for performing a remote ultrasound scan or examination, in accordance with aspects of the present disclosure.

FIG. 3 is a schematic diagram of an ultrasound imaging system 152 for performing a remote ultrasound scan or examination. The ultrasound imaging system 152 includes an ultrasound device 154 including the ultrasound probe 126 as described above in FIG. 2. The ultrasound imaging system 152 also includes the robot 144 described above in FIGS. 1 and 2 having an arm 156 coupled to the ultrasound probe 126.

The ultrasound probe 126 includes a plurality of sensors 157. In certain embodiments, the sensors 157 include a position sensor to determine a force, angle, or position of the ultrasound probe 126. In certain embodiments, the sensors 157 include a pressure sensor to determine a pressure being applied to an acquisition surface of the patient (e.g., subject) by the ultrasound probe 126. In certain embodiments, the sensors 157 may include one or more sensors for monitoring conductive gel or a parameter (e.g., moisture or friction) related to the conductive gel on the acquisition surface of the patient. For example, the sensors 157 may include a moisture sensor to measure a moisture level on the acquisition surface, an in-line force sensor configured to measure friction between the ultrasound probe and the acquisition surface, and/or an optical sensor to optically monitor (e.g., an amount of) the conductive gel on the acquisition surface.

The ultrasound imaging system 152 includes a control system 158. The control system includes a controller 160 located on site with the robot 144 and the ultrasound device 154. The controller 160 is communicatively coupled to and controls the robot and the ultrasound device 154 (e.g., as described in FIGS. 1 and 2). The controller 160 includes a processing system 162 (e.g., one or more processors) and a memory 164. In certain embodiments, the controller 160 may include a central processing unit (CPU), one or more microprocessors, a graphics processing unit (GPU), or other electronic components capable of processing inputted data according to specific logical instructions stored on a memory of the controller or coupled with the controller. Optionally, the controller 160 may include and/or represent one or more hardware circuits or circuitry that include, are connected with, or that both include and are connected with one or more processors, controllers, and/or other hardware logic-based devices. The processing system 162 may execute instructions stored on the memory 164. The memory 164 includes instructions, parameters, algorithms, models, data values, and/or the like utilized by the controller 160 to perform one or more operations described herein (and as described above in FIGS. 1 and 2). The memory 164 may be a tangible and non-transitory computer readable medium such as flash memory, random access memory (RAMI, read-only memory (ROM), electrically erasable program-mable read-only memory (EEPROM), and/or the like. The memory 164 may include a set of machine learning algo-rithms (e.g., convolutional neural network algorithms, deep learning algorithms, decision tree learning algorithms, and/or the like) as described above.

The ultrasound imaging system 152 includes on site of the examination an automatic ultrasound conductive gel dis-penser 161 operably and communicatively coupled to the controller 160. The controller 160 provides control signals to the conductive gel dispenser 161 to automatically apply conductive gel to the acquisition surface in response to a determination that conductive gel should be applied to the acquisition surface of the patient. In certain embodiments, the controller 160 may determine that the conductive gel should be applied based on sensor feedback from one or more of the sensors 157 of the ultrasound probe monitoring conductive gel or a parameter related to the conductive gel on the acquisition surface of the patient. In certain embodi-ments, the controller 160 may utilize machine learning (e.g., artificial intelligence) to analyze image quality of images being acquired during the ultrasound scan of the patient. If the image quality is below a predetermined image quality threshold, then a control signal is provided to conductive gel dispenser 161 to apply conductive gel.

The ultrasound imaging system 152 includes on site of the examination a feedback device 163 (e.g., remote control) that is disposed on (e.g., worn by) or handled by the patient during an ultrasound scan. The feedback device 163 is communicatively coupled to the controller 160. The feed-back device 163 is configured to enable (e.g., via buttons or other input device) the patient to provide input to adjust the pressure applied to the acquisition surface of the subject by the ultrasound probe 126 (via the robot 144). In certain embodiments, the input indicates that the pressure applied to the acquisition surface is making the patient uncomfortable and to reduce the pressure applied or to stop the ultrasound scan. In certain embodiments, the input indicates that the pressure applied to the acquisition surface can be increased. In certain embodiments (e.g., when the robot 144 is autono-mously performing the scan), the patient input may be provided directly to the controller 160 to control the robot 144 to adjust the applied pressure. In certain embodiments, the patient input may be provided to a reverse collaborative robot as described below.

At a remote location 165 (i.e., not in the same room as the patient and possibly many miles away), the control system 158 includes a controller 166. The controller 166 includes a processing system 168 (e.g., one or more processors) and a memory 170. In certain embodiments, the controller 166 may include a central processing unit (CPU), one or more microprocessors, a graphics processing unit (GPU), or other electronic components capable of processing inputted data according to specific logical instructions stored on a memory of the controller or coupled with the controller. Optionally, the controller 166 may include and/or represent one or more hardware circuits or circuitry that include, are connected with, or that both include and are connected with one or more processors, controllers, and/or other hardware logic-based devices. The processing system 162 may execute instructions stored on the memory 170. The memory 170 includes instructions utilized by the controller 166 to per-form one or more operations described herein. The memory 170 may be a tangible and non-transitory computer readable medium such as flash memory, random access memory (RAMI, read-only memory (ROM), electrically erasable programmable read-only memory (EEPROM), and/or the like.

The controller 166 is operably coupled to a display 172 and a user interface 174 at the remote location. The display 172 may include one or more liquid crystal displays (e.g., light emitting diode (LED) backlight), organic light emitting diode (OLED) displays, plasma displays, cathode ray tube (CRT) displays, and/or the like. The display 172 may display patient information, one or more medical images and/or videos, components of a graphical user interface, one or more 2D, 3D, or 4D ultrasound image data sets from ultrasound data stored in the memory 164 or 170 or currently being acquired, measurements, diagnosis, treatment infor-mation, alerts or indications, directions, and/or the like received by the display 1172 from the controller 166.

The user interface 174 controls operations of the control-ler 166 and is configured to receive inputs from the user. The user interface 174 may include a keyboard, a mouse, a touchpad, one or more physical buttons, and/or the like. Optionally, the display 172 may be a touch screen display, which includes at least a portion of the user interface 174. For example, a portion of the user interface 174 may correspond to a graphical user interface (GUI) generated by the controller 166, which is shown on the display 172. The touch screen display can detect a presence of a touch from the operator on the display 172 and can also identify a location of the touch with respect to a surface area of the display 172. For example, the user may select one or more user interface icons of the GUI shown on the display by touching or making contact with the display 172. The touch may be applied by, for example, at least one of an individual's hand, glove, stylus, or the like.

The ultrasound imaging system 152 also includes a reverse collaborative robot 176 at the remote location 165. The reverse collaborative robot 176 is configured to be manipulated by the hand of the user (e.g., clinician or medical technologist). In certain embodiments, the reverse collaborative robot 176 may be an object similar to the ultrasound probe 126 in zero-gravity mode. The reverse collaborative robot 176 is operably coupled to the controller 166 which is operably and communicatively coupled to the controller 160 coupled to the robot 144 coupled to the ultrasound probe 126. The reverse collaborative robot 176 enables the user to control the ultrasound probe 126 that is in contact with the patient via the robot 144.

The reverse collaborative robot 176 comprises a plurality of sensors 178 and actuators 180 (e.g., haptic actuators). The sensors 178 may include a position sensor to determine a force, angle, or position of the reverse collaborative robot 176. The sensors 178 may also include a pressure sensor to determine an amount of pressure or force applied to the reverse collaborative robot 176 by the hand of the user. The actuators 180 in response to feedback signals from the control system 158 may transmit the force, angle, and position of the ultrasound probe 126. In addition, the actuators 180 may simulate a pressure in the reverse collaborative robot of the pressure being applied by the ultrasound probe 126 (via the robot 144) on the acquisition surface of the patient. Thus, ultrasound imaging system 152 forms a two-way haptic sensing between the ultrasound probe 126 (being moved by the robot 144) and the reverse collaborative robot 176.

In addition, the actuators 180 in response to feedback signals may provide an alert, via haptic feedback (e.g., vibrotactile feedback, tactile feedback, force feedback, etc.), to adjust the pressure applied to the patient. The alert may be triggered by the patient via input provided by the feedback device 163. The alert may indicate that that the pressure applied to the acquisition surface of the patient is making the patient uncomfortable and to reduce the pressure applied or to stop the ultrasound scan. In certain embodiments, the alert indicates that the pressure applied to the acquisition surface can be increased. Different alerts may be provided by different haptic feedback and/or different patterns of haptic feedback.

In certain embodiments, the alert may be triggered by one of the sensors 157 (e.g., pressure sensor) of the ultrasound probe 126. In particular, the control system 158 based on the feedback from the pressure sensor may provide the alert, via the actuators 180, to the user to move or to apply more pressure to the ultrasound probe 126, via the reverse collaborative robot 176, to create full ultrasound probe contact with the acquisition surface. In certain embodiments, the alert may be triggered by the control system 158, where the control system 158 may utilize machine learning (e.g., artificial intelligence) to analyze image quality of images being acquired during the ultrasound scan of the patient. If the image quality is below a predetermined image quality threshold, then the alert is provided, via the actuators 180, to the user to move or to apply more pressure to the ultrasound probe 126, via the reverse collaborative robot 176, to create full ultrasound probe contact with the acquisition surface. In certain embodiments (e.g., when the robot 144 is autonomously performing the scan), the determination (via sensor feedback or image quality analysis) to move or apply more pressure to the ultrasound probe may be provided directly to the controller 160 to control the robot 144 to adjust the applied pressure.

In certain embodiments, the ultrasound imaging system 152 may be utilized for remote ultrasound scanning without utilizing the reverse collaborative robot 176. Instead, the user (e.g., clinician or medical technologist) at the remote location 165 may initiate the ultrasound scan via an input to the user interface 174 and the robot 144 may autonomously perform the entire ultrasound scan. The user can view the acquired images on the display 172. The user may also remotely provide an input selecting the scan protocol and region to anatomical region to perform the ultrasound scan that is performed autonomously by the robot 144. The robot 144 may be trained to autonomously perform the ultrasound scan as discussed above.

FIG. 4 illustrates a flow diagram of a method 182 for performing a remote ultrasound exam (e.g., utilizing reverse collaborative robot). One or more steps of the method 182 may be performed by one or more components of the ultrasound imaging system 152 in FIG. 3 (e.g., control system 158).

The method 182 includes receiving input from a user, via a user interface, to begin an ultrasound scan of a subject utilizing a robot having an arm coupled to an ultrasound probe of an ultrasound device to move the ultrasound probe along an acquisition surface of the subject (e.g., patient), wherein the user is located at a location remote from both the ultrasound device and the robot (block 184). The method 182 also includes beginning a remote ultrasound scan of the subject (block 186). The method 182 further includes providing, via the control system, control signals to the robot to move the ultrasound probe along the acquisition surface during the ultrasound scan to acquire ultrasound scan data in response to manipulation of a reverse collaborative robot by a hand of the user, wherein the reverse collaborative robot is located at the location remote from both the ultrasound device and the robot (block 188). In certain embodiments, the remote ultrasound sensing system has two-haptic sensing as described above. In certain embodiments, the method 182 includes providing feedback signals to the reverse collaborative robot that cause the actuators to simulate a pressure applied to the acquisition surface of the subject by the ultrasound probe (block 190). In certain embodiments, the method 182 includes providing control signals to the robot to adjust the pressure applied to the acquisition surface of the subject based on a user pressure applied to the reverse collaborative robot by the hand of the user (block 192).

Figure 5:
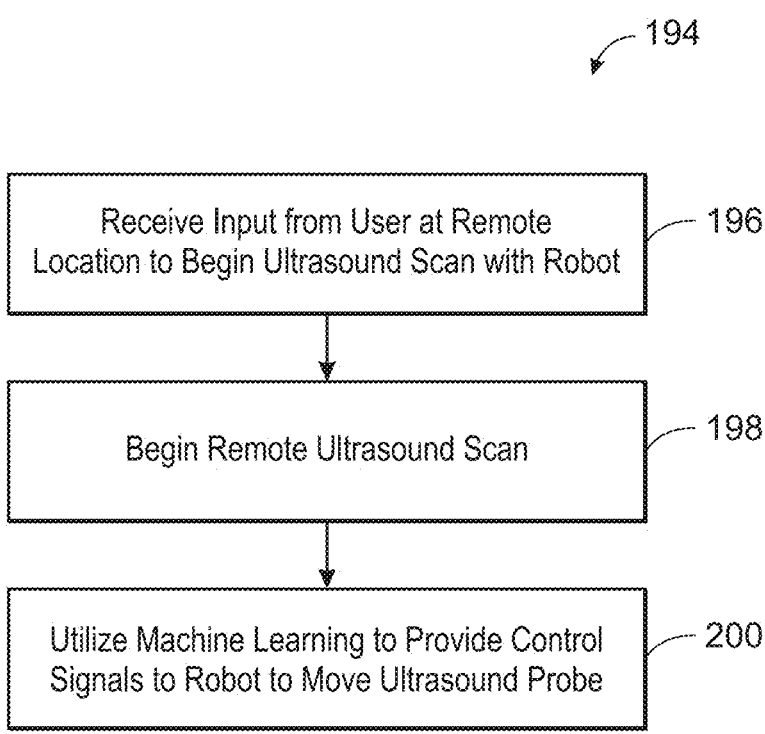
FIG. 5 illustrates a flow diagram of a method for performing a remote ultrasound exam (e.g., utilizing a robot autonomously), in accordance with aspects of the present disclosure.

FIG. 5 illustrates a flow diagram of a method 194 for performing a remote ultrasound exam (e.g., utilizing robot autonomously). One or more steps of the method 194 may be performed by one or more components of the ultrasound imaging system 152 in FIG. 3 (e.g., control system 158).

The method 194 includes receiving input from a user, via a user interface, to begin an ultrasound scan of a subject utilizing a robot having an arm coupled to an ultrasound probe of an ultrasound device to move the ultrasound probe along an acquisition surface of the subject (e.g., patient), wherein the user is located at a location remote from both the ultrasound device and the robot (block 196). The method 194 also includes beginning a remote ultrasound scan of the subject (block 198). The method 194 also includes utilizing machine learning to provide control signals to the robot to move the ultrasound probe along the acquisition surface during the ultrasound scan to acquire ultrasound scan data free of interaction from the user (block 200). Thus, the robot, via the machine learning, performs the ultrasound scan autonomously.

Figure 6:
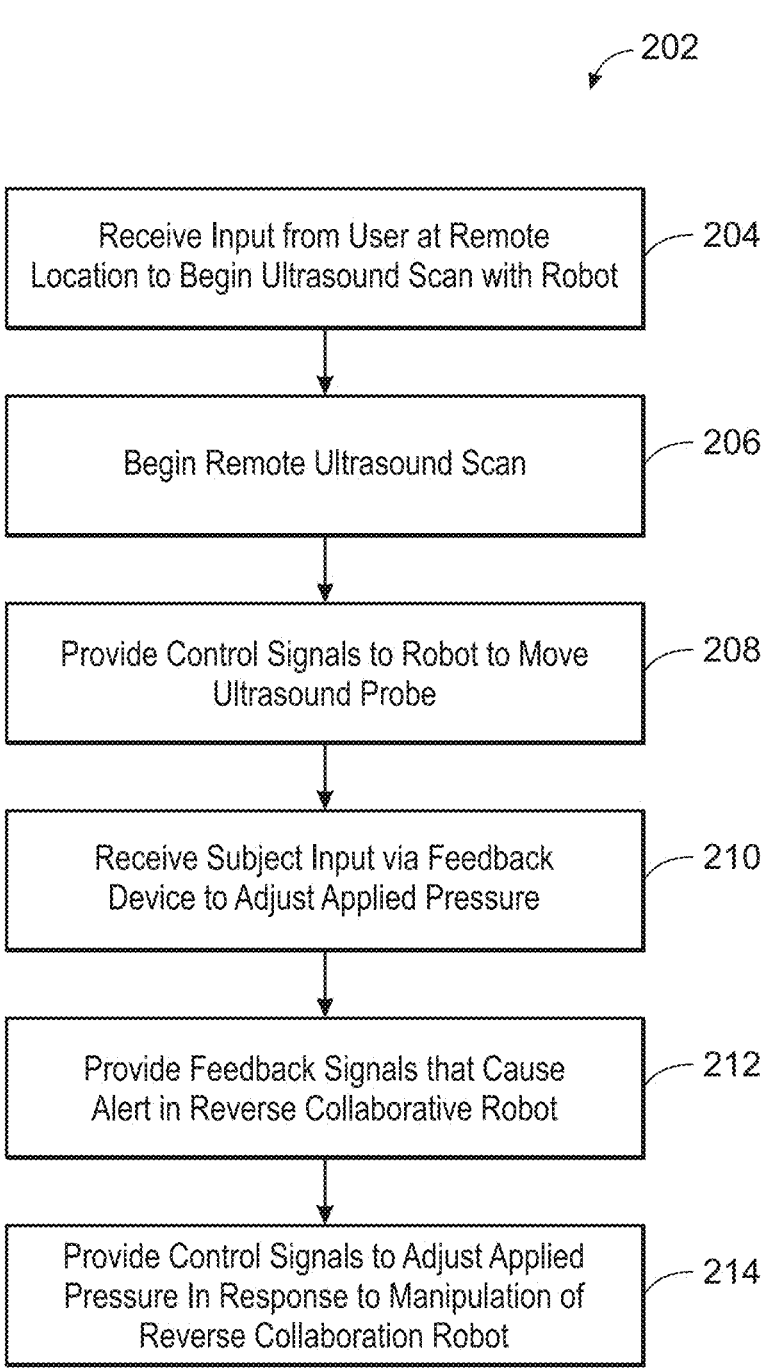
FIG. 6 illustrates a flow diagram of a method for performing a remote ultrasound exam with patient feedback (e.g., utilizing the reverse collaborative robot), in accordance with aspects of the present disclosure.

FIG. 6 illustrates a flow diagram of a method 202 for performing a remote ultrasound exam with patient feedback (e.g., utilizing the reverse collaborative robot). One or more steps of the method 202 may be performed by one or more components of the ultrasound imaging system 152 in FIG. 3 (e.g., control system 158).

The method 202 includes receiving input from a user, via a user interface, to begin an ultrasound scan of a subject utilizing a robot having an arm coupled to an ultrasound probe of an ultrasound device to move the ultrasound probe along an acquisition surface of the subject (e.g., patient), wherein the user is located at a location remote from both the ultrasound device and the robot (block 204). The method 202 also includes beginning a remote ultrasound scan of the subject (block 206). The method 202 also includes providing control signals to the robot to move the ultrasound probe along the acquisition surface during the ultrasound scan to acquire ultrasound scan data in response to manipulation of a reverse collaborative robot by a hand of the user, wherein the reverse collaborative robot is located at the location remote from both the ultrasound device and the robot (block 208). The method 202 includes receiving subject input, via a feedback device (e.g., disposed on or handled by subject), to adjust the pressure applied to the acquisition surface of the subject by the ultrasound probe (block 210). The method 202 also includes providing feedback signals, in response to the subject input (e.g., via the feedback device 163), to the reverse collaborative robot that cause the actuators to provide an alert to the user to alter the pressure applied to the acquisition surface of the subject by the ultrasound probe (block 212). Additionally or alternatively, the feedback signals provide an alert to the user via a user interface and/or cause the collaborative robot to automatically adjust the pressure applied to the acquisition surface of the user by the ultrasound probe, which may include stopping or pausing the examination. The method 202 further includes providing control signals to the robot to adjust the pressure applied to the acquisition surface of the subject by the ultrasound probe in response to manipulation of the reverse collaboration robot by the user (block 214). In certain embodiments, the subject input is an indication to decrease the pressure or stop the examination. In certain embodiments, the subject input is an indication to increase the pressure.

Figure 7:
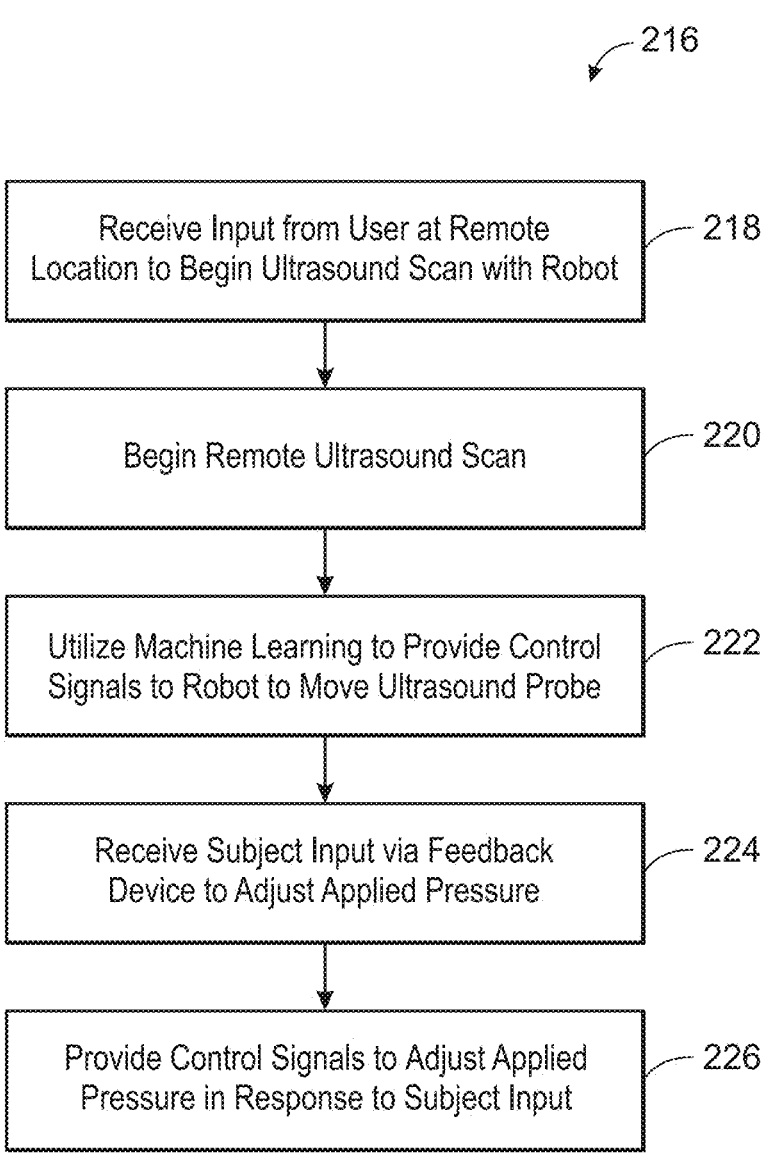
FIG. 7 illustrates a flow diagram of a method for performing a remote ultrasound exam with patient feedback (e.g., utilizing a robot autonomously), in accordance with aspects of the present disclosure.

FIG. 7 illustrates a flow diagram of a method 216 for performing a remote ultrasound exam with patient feedback (e.g., utilizing the robot autonomously). One or more steps of the method 216 may be performed by one or more components of the ultrasound imaging system 152 in FIG. 3 (e.g., control system 158).

The method 216 includes receiving input from a user, via a user interface, to begin an ultrasound scan of a subject utilizing a robot having an arm coupled to an ultrasound probe of an ultrasound device to move the ultrasound probe along an acquisition surface of the subject (e.g., patient), wherein the user is located at a location remote from both the ultrasound device and the robot (block 218). The method 216 also includes beginning a remote ultrasound scan of the subject (block 220). The method 216 also includes utilizing machine learning to provide control signals to the robot to move the ultrasound probe along the acquisition surface during the ultrasound scan to acquire ultrasound scan data free of interaction from the user (block 222). The method 216 includes receiving subject input, via a feedback device (e.g., disposed on or handled by subject), to adjust the pressure applied to the acquisition surface of the subject by the ultrasound probe (block 224). The method 216 further includes providing control signals to the robot to adjust the pressure applied to the acquisition surface of the subject by the ultrasound probe in response the subject input (block 226). In certain embodiments, the subject input is an indication to decrease the pressure or stop the examination. In certain embodiments, the subject input is an indication to increase the pressure.

Figure 8:
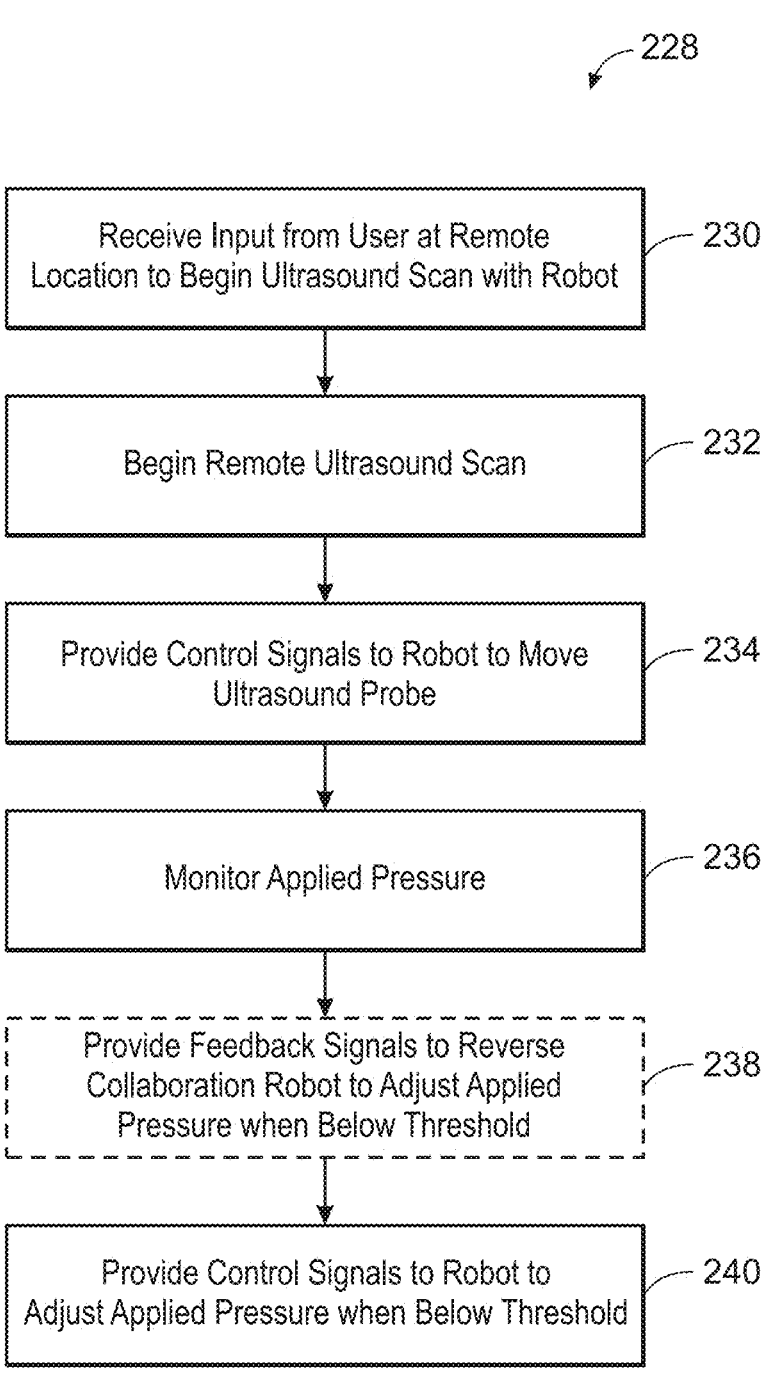
FIG. 8 illustrates a flow diagram of a method for performing a remote ultrasound exam with applied pressure monitoring (e.g., utilizing sensor feedback), in accordance with aspects of the present disclosure.

FIG. 8 illustrates a flow diagram of a method 228 for performing a remote ultrasound exam with applied pressure monitoring (e.g., utilizing sensor feedback). One or more steps of the method 228 may be performed by one or more components of the ultrasound imaging system 152 in FIG. 3 (e.g., control system 158).

The method 228 includes receiving input from a user, via a user interface, to begin an ultrasound scan of a subject utilizing a robot having an arm coupled to an ultrasound probe of an ultrasound device to move the ultrasound probe along an acquisition surface of the subject (e.g., patient), wherein the user is located at a location remote from both the ultrasound device and the robot (block 230). The method 228 also includes beginning a remote ultrasound scan of the subject (block 232). The method 228 also includes providing control signals to the robot to move the ultrasound probe along the acquisition surface during the ultrasound scan to acquire ultrasound scan data (block 234). In certain embodiments, the control signals may derive from remote manipulation of the reverse collaboration robot by the user as described in the method 182 in FIG. 4. In certain embodiments, the control signals may derive from machine learning control of the robot as described in the method 194 in FIG. 5. The method 228 includes monitoring the applied pressure/force to the acquisition surface of the subject based on feedback from one or more sensors (e.g., pressure sensors) in the ultrasound probe (block 236). In certain embodiments, the method 228 includes providing feedback signals to the reverse collaboration robot that cause the actuators to provide an alert to the user to move or to apply more pressure to the ultrasound probe, via the reverse collaborative robot, to create full ultrasound probe contact with the acquisition surface when the measured applied pressure is below a predetermined pressure threshold (block 238). The method 228 includes providing control signals to move or apply more pressure to the ultrasound probe to create full ultrasound probe contact with the acquisition surface when the measured applied pressure is below a predetermined pressure threshold (block 240). In certain embodiments, the control signals are derived from manipulation of the reverse collaboration robot in response to the alert. In certain embodiments, the control are derived directly from the control system in response to the sensor feedback.

FIG. 9 illustrates a flow diagram of a method 242 for performing a remote ultrasound exam with applied pressure monitoring (e.g., utilizing analysis of image quality). One or more steps of the method 242 may be performed by one or more components of the ultrasound imaging system 152 in FIG. 3 (e.g., control system 158).

The method 242 includes receiving input from a user, via a user interface, to begin an ultrasound scan of a subject utilizing a robot having an arm coupled to an ultrasound probe of an ultrasound device to move the ultrasound probe along an acquisition surface of the subject (e.g., patient), wherein the user is located at a location remote from both the ultrasound device and the robot (block 244). The method 242 also includes beginning a remote ultrasound scan of the subject (block 246). The method 242 also includes providing control signals to the robot to move the ultrasound probe along the acquisition surface during the ultrasound scan to acquire ultrasound scan data (block 248). In certain embodiments, the control signals may derive from remote manipulation of the reverse collaboration robot by the user as described in the method 182 in FIG. 4. In certain embodiments, the control signals may derive from machine learning control of the robot as described in the method 194 in FIG. 5. The method 242 includes obtaining images from the ultrasound scan (block 250). The method 242 also includes analyzing the image quality of the obtained images (block 252). In certain embodiments, the method 242 includes providing feedback signals to the reverse collaboration robot that cause the actuators to provide an alert to the user to move or to apply more pressure to the ultrasound probe, via the reverse collaborative robot, to create full ultrasound probe contact with the acquisition surface when the image quality of one or more of the images is below a predetermined image quality threshold (block 254). The method 242 includes providing control signals to move or apply more pressure to the ultrasound probe to create full ultrasound probe contact with the acquisition surface when the image quality of one or more of the images is below a predetermined image quality threshold (block 256). In certain embodiments, the control signals are derived from manipulation of the reverse collaboration robot in response to the alert. In certain embodiments, the control are derived directly from the control system in response to the sensor feedback.

Figure 10:
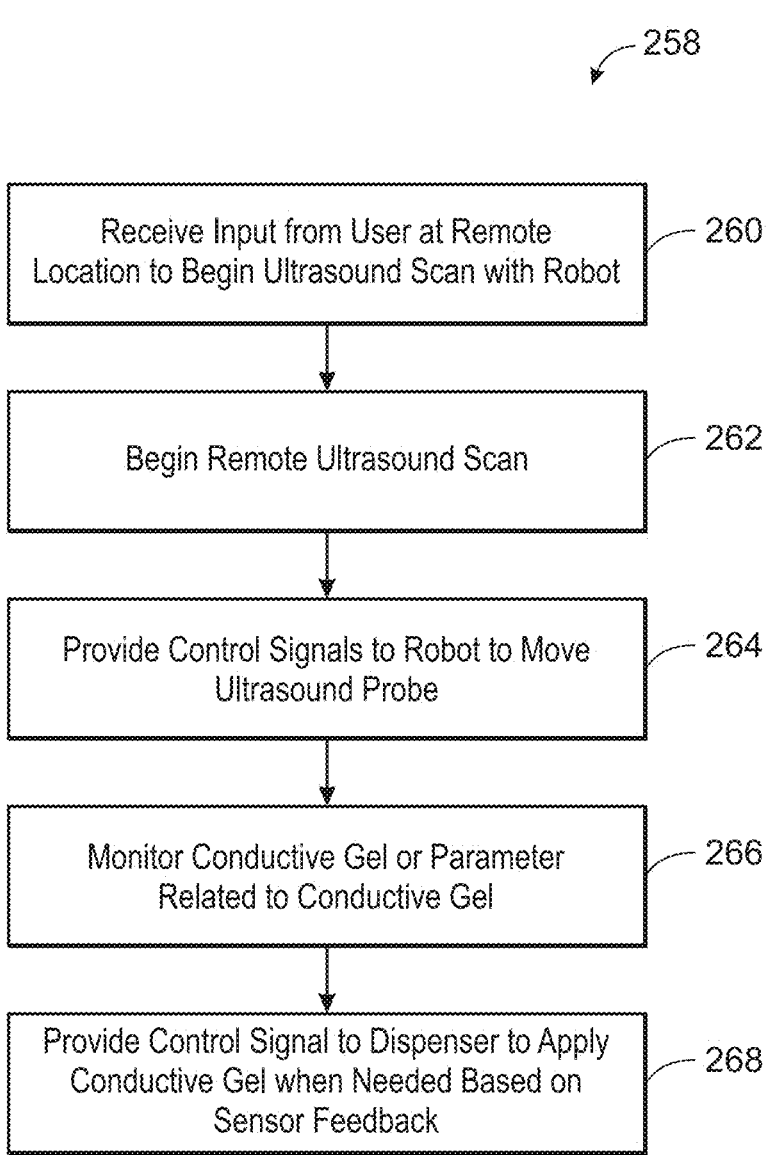
FIG. 10 illustrates a flow diagram of a method for performing a remote ultrasound exam with conductive gel monitoring (e.g., utilizing sensor feedback), in accordance with aspects of the present disclosure.

FIG. 10 illustrates a flow diagram of a method 258 for performing a remote ultrasound exam with conductive gel monitoring (e.g., utilizing sensor feedback). One or more steps of the method 258 may be performed by one or more components of the ultrasound imaging system 152 in FIG. 3 (e.g., control system 158).

The method 258 includes receiving input from a user, via a user interface, to begin an ultrasound scan of a subject utilizing a robot having an arm coupled to an ultrasound probe of an ultrasound device to move the ultrasound probe along an acquisition surface of the subject (e.g., patient), wherein the user is located at a location remote from both the ultrasound device and the robot (block 260). The method 258 also includes beginning a remote ultrasound scan of the subject (block 262). The method 258 also includes providing control signals to the robot to move the ultrasound probe along the acquisition surface during the ultrasound scan to acquire ultrasound scan data (block 264). In certain embodiments, the control signals may derive from remote manipulation of the reverse collaboration robot by the user as described in the method 182 in FIG. 4. In certain embodiments, the control signals may derive from machine learning control of the robot as described in the method 194 in FIG. 5. The method 258 includes monitoring the conductive gel or a parameter related to the conductive gel on the acquisition surface based on feedback from one or more sensors (e.g., moisture sensors, friction sensors, optical sensors, etc.) in the ultrasound probe (block 266). The method 258 includes providing a control signal to an automatic ultrasound conductive gel dispenser to apply conductive gel to the acquisition surface of the subject when additional conductive gel is needed based on the sensor feedback from the sensor (block 268).

Figure 11:
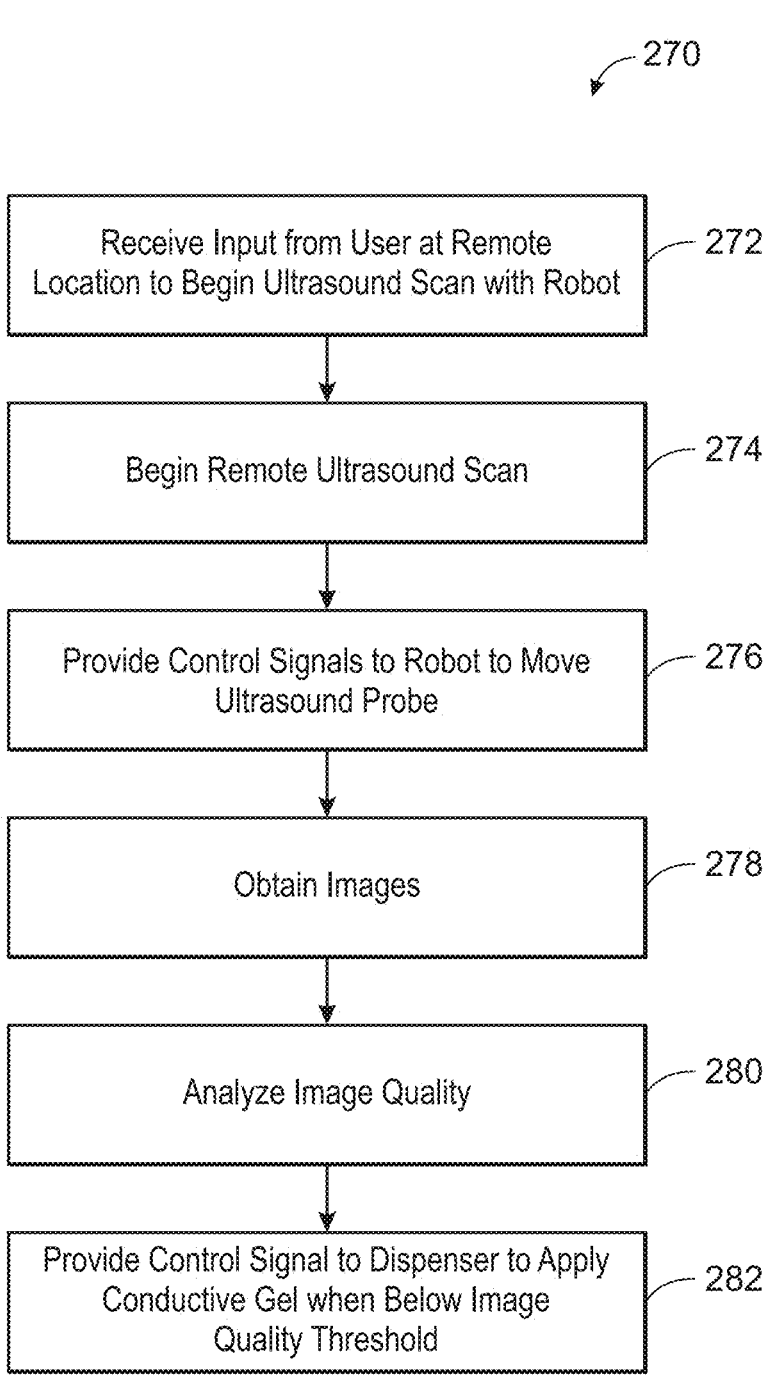
FIG. 11 illustrates a flow diagram of a method for performing a remote ultrasound exam with conductive gel monitoring (e.g., utilizing analysis of image quality), in accordance with aspects of the present disclosure.

FIG. 11 illustrates a flow diagram of a method 270 for performing a remote ultrasound exam with conductive gel monitoring (e.g., utilizing analysis of image quality) One or more steps of the method 270 may be performed by one or more components of the ultrasound imaging system 152 in FIG. 3 (e.g., control system 158).

The method 270 includes receiving input from a user, via a user interface, to begin an ultrasound scan of a subject utilizing a robot having an arm coupled to an ultrasound probe of an ultrasound device to move the ultrasound probe along an acquisition surface of the subject (e.g., patient), wherein the user is located at a location remote from both the ultrasound device and the robot (block 272). The method 270 also includes beginning a remote ultrasound scan of the subject (block 274). The method 270 also includes providing control signals to the robot to move the ultrasound probe along the acquisition surface during the ultrasound scan to acquire ultrasound scan data (block 276). In certain embodiments, the control signals may derive from remote manipulation of the reverse collaboration robot by the user as described in the method 182 in FIG. 4. In certain embodiments, the control signals may derive from machine learning control of the robot as described in the method 194 in FIG. 5. The method 270 includes obtaining images from the ultrasound scan (block 278). The method 270 also includes analyzing the image quality of the obtained images (block 280). The method 270 includes providing a control signal to an automatic ultrasound conductive gel dispenser to apply conductive gel to the acquisition surface of the subject when the image quality of one or more of the images is below a predetermined image quality threshold (block 282).

Technical effects of the disclosed embodiments include providing systems and methods for remote ultrasound scanning utilizing a robotic system. Technical effects of the disclosed embodiments includer providing a two-way haptic sensing system for use with robotic ultrasound scanning. Technical effects of the disclosed embodiments include providing more access to ultrasound examinations in remote areas where specialized clinicians or medical technologists are not available. The disclosed embodiments also providing the patient with the ability to control their comfort level while also providing an extra layer of safety for remote imaging.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform] ing [a function] . . . ", it is intended that such elements are to be interpreted under 35 U.S.C. 112 (f). However, for any claims containing elements designated in any other manner, it is intended that such elements are not to be interpreted under 35 U.S.C. 112 (f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:
1. A system, comprising:
an ultrasound device comprising an ultrasound probe;

a robot comprising an arm configured to couple to the ultrasound probe;

a reverse collaborative robot configured to be manipulated by a user, wherein the reverse collaborative robot is located at a location remote from both the ultrasound device and the robot, and wherein the reverse collaborative robot comprises actuators configured to provide haptic feedback to the user;

a feedback device disposed on or handled by a subject being imaged by the ultrasound device, wherein the feedback device is configured to receive input from the subject via an input device on the feedback device to adjust a pressure applied to an acquisition surface of the subject being imaged by the ultrasound probe; and a control system comprising a processing system and memory, wherein the control system is configured to:

receive input from the user, via a user interface, to begin an ultrasound scan of the subject utilizing the robot to move the ultrasound probe along the acquisition surface of the subject, wherein the user is located at the location remote from both the ultrasound device and the robot;

provide control signals to the robot to move the ultrasound probe along the acquisition surface during the ultrasound scan to acquire ultrasound scan data in response to manipulation of the reverse collaborative robot by the user; and provide feedback signals to the reverse collaborative robot or the user interface to change a pressure applied to the acquisition surface of the subject by the ultrasound probe; and provide the feedback signals, in response to the subject input via the feedback device, to the reverse collaborative robot that cause the actuators to provide an alert to the user to alter the pressure applied to the acquisition surface of the subject by the ultrasound probe.

2. The system of claim 1, wherein the subject input is configured to indicate that the pressure applied to the acquisition surface is making the subject uncomfortable and to reduce the pressure applied to the acquisition surface or to stop the ultrasound scan.

3. The system of claim 1, wherein the subject input is configured to indicate that the pressure applied to the acquisition surface can be increased.

4. The system of claim 1, wherein the control system is further configured to utilize machine learning to analyze image quality of images acquired during the ultrasound scan and to provide the feedback signals, when the image quality is below a predetermined image quality threshold, to the reverse collaborative robot that cause the actuators to provide an alert to the user to move or to apply more pressure to the ultrasound probe, via the reverse collaborative robot, to create full ultrasound probe contact with the acquisition surface.

5. The system of claim 1, wherein the ultrasound probe comprises a pressure sensor configured to measure the pressure applied to the acquisition surface, and wherein the control system is further configured to provide the feedback signals, when the pressure applied as measured by the pressure sensor is below a predetermined pressure threshold, to the reverse collaborative robot that cause the actuators to provide an alert to the user to move or to apply more pressure to the ultrasound probe, via the reverse collaborative robot, to create full ultrasound probe contact with the acquisition surface.

6. The system of claim 1, further comprising an automatic ultrasound conductive gel dispenser communicatively coupled to the control system, wherein the control system is further configured to utilize machine learning to analyze image quality of images acquired during the ultrasound scan and to provide a control signal, when the image quality is below a predetermined image quality threshold, to the automatic ultrasound conductive gel dispenser to apply conductive gel to the acquisition surface of the subject.

7. The system of claim 1, further comprising an automatic ultrasound conductive gel dispenser communicatively coupled to the control system, wherein the ultrasound probe comprises a sensor configured to monitor conductive gel or a parameter related to the conductive gel on the acquisition surface, and wherein the control system is further configured to provide a control signal to the automatic ultrasound conductive gel dispenser to apply conductive gel to the acquisition surface of the subject when additional conductive gel is needed based on sensor feedback from the sensor.

8. The system of claim 7, wherein the sensor comprises an optical sensor to optically monitor the conductive gel on the acquisition surface, a moisture sensor configured to measure a moisture level on the acquisition surface, or an in-line force sensor configured to measure friction between the ultrasound probe and the acquisition surface.

9. A system, comprising:

an ultrasound device comprising an ultrasound probe;

a robot comprising an arm configured to couple to the ultrasound probe; and a control system comprising a processing system and memory, wherein the control system is configured to:

receive input from a user, via a user interface, to begin an ultrasound scan of a subject utilizing the robot to move the ultrasound probe along an acquisition surface of the subject, wherein the user is located at a location remote from both the ultrasound device and the robot;

utilize machine learning to provide control signals to the robot to move the ultrasound probe along the acquisition surface during the ultrasound scan to acquire ultrasound scan data free of interaction from the user; and utilize machine learning to analyze image quality of images acquired during the ultrasound scan and to provide the control signals, when the image quality is below a predetermined image quality threshold, to the robot to move or to apply more pressure to the ultrasound probe to create full ultrasound probe contact with the acquisition surface.

10. The system of claim 9, further comprising a feedback device disposed on or handled by the subject, wherein the feedback device is configured to receive subject input to adjust the pressure applied to the acquisition surface of the subject by the ultrasound probe.

11. The system of claim 10, wherein the subject input is configured to indicate that the pressure applied to the acquisition surface is making the subject uncomfortable and to reduce the pressure applied to the acquisition surface or to stop the ultrasound scan or the subject input indicates that the pressure applied to the acquisition surface can be increased.

12. The system of claim 10, further comprising an automatic ultrasound conductive gel dispenser communicatively coupled to the control system, wherein the control system is further configured to utilize machine learning to analyze image quality of images acquired during the ultrasound scan and to provide a control signal, when the image quality is below the predetermined image quality threshold, to the automatic ultrasound conductive gel dispenser to apply conductive gel to the acquisition surface of the subject.

13. The system of claim 9, wherein the ultrasound probe comprises a pressure sensor configured to measure the pressure applied to the acquisition surface, and wherein the control system is further configured to provide the control signals, when the pressure applied as measured by the pressure sensor is below a predetermined pressure threshold, to the robot to move or to apply more pressure to the ultrasound probe to create full ultrasound probe contact with the acquisition surface.

14. The system of claim 9, further comprising an automatic ultrasound conductive gel dispenser communicatively coupled to the control system, wherein the ultrasound probe comprises a sensor configured to monitor conductive gel or a parameter related to the conductive gel on the acquisition surface, and wherein the control system is further configured to provide a control signal to the automatic ultrasound conductive gel dispenser to apply conductive gel to the acquisition surface of the subject when additional conductive gel is needed based on sensor feedback from the sensor.

15. The system of claim 14, wherein the sensor comprises an optical sensor to optically monitor the conductive gel on the acquisition surface, a moisture sensor configured to measure a moisture level on the acquisition surface, or an in-line force sensor configured to measure friction between the ultrasound probe and the acquisition surface.

16. The system of claim 9, wherein the control system is configured to utilize machine learning to define an anatomical structure model to identify one or more anatomical features of interest based on one or more anatomical structures within the images acquired during the ultrasound scan.

17. A method for performing a remote ultrasound exam, comprising:

receiving, at a control system having a processing system and memory, input from a user, via a user interface, to begin an ultrasound scan of a subject utilizing a robot having an arm coupled to an ultrasound probe of an ultrasound device to move the ultrasound probe along an acquisition surface of the subject, wherein the user is located at a location remote from both the ultrasound device and the robot;

providing, via the control system, control signals to the robot to move the ultrasound probe along the acquisition surface during the ultrasound scan to acquire ultrasound scan data in response to manipulation of a reverse collaborative robot by the user, wherein the reverse collaborative robot is located at the location remote from both the ultrasound device and the robot, and wherein the reverse collaborative robot comprises actuators configured to provide haptic feedback to the user; and utilizing, via the control system, machine learning to analyze image quality of images acquired during the ultrasound scan and to provide feedback signals, when the image quality is below a predetermined image quality threshold, to the reverse collaborative robot that cause the actuators to provide an alert to the user to move or to apply more pressure to the ultrasound probe, via the reverse collaborative robot, to create full ultrasound probe contact with the acquisition surface.

18. The method of claim 17, wherein the ultrasound probe comprises a pressure sensor configured to measure the pressure applied to the acquisition surface, and wherein the method further comprises providing, via the control system, the feedback signals, when the pressure applied as measured by the pressure sensor is below a predetermined pressure threshold, to the reverse collaborative robot that cause the actuators to provide an alert to the user to move or to apply more pressure to the ultrasound probe, via the reverse collaborative robot, to create full ultrasound probe contact with the acquisition surface.

19. The method of claim 17, further comprising utilizing, via the control system, machine learning to analyze image quality of images acquired during the ultrasound scan and to provide a control signal, when the image quality is below the predetermined image quality threshold, to an automatic ultrasound conductive gel dispenser, communicatively coupled to the control system, to apply conductive gel to the acquisition surface of the subject.

20. The method of claim 17, further comprising utilizing, via the control system, machine learning to define an anatomical structure model for identifying anatomical features of interest within the images acquired during the ultrasound scan by automatically building a statistical model or a database of true positives and true negatives corresponding to each anatomical structure identified based on features from a set of training images, a classification model, or supervised modeling.

\* \* \* \* \*